United States Patent [19]
Chace et al.

[11] Patent Number: 5,949,069
[45] Date of Patent: Sep. 7, 1999

[54] METHOD AND APPARATUS FOR MEASURING VOLUMETRIC WATER FLOW RATES IN HIGHLY INCLINED WELLBORES

[75] Inventors: David M. Chace; Darryl E. Trcka, both of Houston, Tex.; Rene W. Mayer, Abu Dhabi, United Arab Emirates

[73] Assignee: Western Atlas International, Inc., Houston, Tex.

[21] Appl. No.: 08/970,253

[22] Filed: Nov. 14, 1997

[51] Int. Cl.$^6$ .................................. G01V 5/10; G01F 1/00
[52] U.S. Cl. .................................... 250/269.7; 250/356.1; 250/269.8; 250/269.1; 250/256
[58] Field of Search .............................. 250/269.7, 269.1, 250/269.8, 302, 303, 256, 356.1, 356.2

[56] References Cited

U.S. PATENT DOCUMENTS

| | | | |
|---|---|---|---|
| 5,219,518 | 6/1993 | McKeon et al. | 376/166 |
| 5,404,752 | 4/1995 | Chace et al. | 73/152.14 |
| 5,552,598 | 9/1996 | Kessler et al. | 250/269.3 |
| 5,708,203 | 1/1998 | McKinley et al. | 73/152.04 |
| 5,825,024 | 10/1998 | Badruzzaman | 250/269.6 |

OTHER PUBLICATIONS

"Interpretive Methods for Production Well Logs," instructional manual on interpretation of production well logging measurements, Western Atlas Logging Services, Houston, TX (1982) (pp. 87,99–100).

"Measuring Three–Phase Holdups in Horizontal Wellbores Using Pulsed Neutron Instruments," D. Rtcka et al., paper No. 36561, Society of Petroleum Engineers, Richardson, TX (1996).

*Primary Examiner*—Constantine Hannaher
*Assistant Examiner*—Albert Gagliardi
*Attorney, Agent, or Firm*—Richard A. Fagin

[57] ABSTRACT

A method for determining a volume fraction of water moving in a predetermined direction along a highly inclined conduit. The method includes measuring a fractional volume of water occupying the conduit at a plurality of locations along the conduit. An oxygen activation velocity of the water flowing in the conduit is determined at a plurality of locations along the conduit. A counting rate of a gamma ray detector used to measure oxygen activation is normalized with respect to the measured fractional volume of water. The normalized count rates of the gamma ray detector are characterized with respect to a relative velocity between the water and the detector. The step of characterizing is performed in portions of the conduit which are sloped so that gravity acts on the water along the predetermined direction. A fraction of the characterized counting rate represented by the oxygen activation counting rates measured along the conduit is determined. The fraction represents the fractional volume of water moving in the predetermined direction.

5 Claims, 3 Drawing Sheets

METHOD AND APPARATUS FOR MEASURING VOLUMETRIC WATER FLOW RATES IN HIGHLY INCLINED WELLBORES

BACKGROUND OF THE INVENTION

1. Field of the Invention

The invention is related to the field of production logging of oil and gas wells. More specifically, the invention is related to methods and apparatus for measuring the volumetric flow rates of water in highly inclined or horizontal wellbores, where in portions of such wellbores some of the water may be flowing in a direction away from the wellhead.

2. Description of the Related Art

Highly inclined and horizontal wellbores are drilled for the purpose of more efficiently extracting petroleum from reservoirs in earth formations than is generally possible using vertical wellbores. The increase in efficiency is related to the length of the wellbore which penetrates the petroleum-bearing portion of the earth formation. Since many petroleum reservoirs are segregated by gravity and have large lateral extent with respect to their vertical aspect, highly inclined or horizontal wellbores enable having a very long wellbore length through the petroleum-bearing portion of the reservoir.

The typical highly inclined or horizontal wellbore does not penetrate straight through the reservoir, however. When a highly inclined or horizontal wellbore is drilled, the drilling operator typically will have to make adjustments to the drilling direction to maintain the wellbore trajectory within the desired part of the particular reservoir. As a result of these trajectory adjustments, the typical highly inclined or horizontal wellbore will undulate about the intended trajectory and therefore can have sections which are inclined more than 90° deviation from vertical. This means that while the measured depth of the wellbore (this usually being defined as the length of the wellbore from its termination at the earth's surface at a "wellhead") is increasing, the true vertical depth (defined as the absolute vertical distance to the earth's surface from any point in the wellbore) is actually decreasing over such sections of the wellbore. As the wellbore trajectory is returned to the desired position within the reservoir, the inclination may be "dropped" by the drilling operator to continue drilling the wellbore at a particular true vertical depth, creating an undulation. The undulated sections of the wellbore having segments at above 90° inclination can form gravity "traps" for more dense fluids such as water, which may be produced from the reservoir when the wellbore is completed.

Various production logging methods are known in the art for identifying zones in a reservoir (or the reservoirs in a wellbore which penetrates multiple reservoirs) which cause water to be introduced into the wellbore. The production logging methods known in the art enable the wellbore operator to determine the volumetric flow rates of water into the wellbore from any interval traversed by the production logging instrumentation. Most production logging methods known in the art, which include various velocity measuring devices such as the "spinner" flowmeter, do not easily resolve whether some of the water in a horizontal wellbore is stagnant or flowing "backwards", that is, in a direction away from the wellhead. Such a flow direction is possible particularly near the previously described "traps", in the segments of the wellbore having inclination above 90°. The limitations on prior art production logging methods are primarily because the velocity measurements made by devices such as the spinner flowmeter are localized to the position of the instrument itself within the cross-section of the wellbore. Near traps, some of the water may be flowing away from the wellhead due to gravity, while other portions of the water may be flowing towards the wellhead. The true volumetric flow rate of water towards the wellhead may not be correctly measured by spinner flowmeters or other "localized" velocity measuring devices.

One method for determining the volumetric flow rate of water irrespective of internal turbulences, or the presence of other fluids in the flow stream such as oil and gas, is known as "oxygen activation" logging. Oxygen activation logging is described, for example, in U.S. Pat. No. 5,461,909 issued to Arnold or in U.S. Pat. No. 5,404,752 issued to Chace et al. Generally speaking, the method described in these patents includes bombarding the fluid in the wellbore with bursts of high energy neutrons, and detecting gamma rays which are characteristic of oxygen which has been "activated" by the high energy neutrons. The rates at which the gamma rays are detected at one or more detectors spaced apart from the neutron source is related to the velocity of the water moving past the logging instrument.

A method for determining the flow rate of water where there is more than one "phase" ("phase" referring to a fluid component such as oil or gas) in the fluid moving through the wellbore is described in U.S. Pat. No. 5,306,911 issued to Hunt. The method in the Hunt '911 patent includes measuring the oxygen-activation gamma rays at a fixed position within the wellbore for a period of time and determining the water flow rate by characterizing the time-based measurements of gamma rays with respect to water flow rate. A significant limitation of the method described in the Hunt '911 patent is that it requires keeping the logging instrument stationary within the wellbore to make the time-based gamma ray measurements. In a horizontal or highly inclined wellbore where several thousand feet of wellbore may need to be evaluated to determine the zones causing the water production, the method in the Hunt '911 patent would be impracticable.

What is needed is a method for measuring flow rates of water in highly inclined or horizontal wellbores which enables substantially continuous movement of the logging instrument through the wellbore.

SUMMARY OF THE INVENTION

The invention is a method for determining the volumetric fraction of water moving in a predetermined direction along a highly inclined conduit. The method includes the step of measuring a fractional volume of water occupying the conduit at a plurality of locations along the conduit. An oxygen activation velocity of the water flowing in the conduit is also determined at a plurality of locations along the conduit. A counting rate of a gamma ray detector used to measure oxygen activation is normalized with respect to the measured fractional volume of water. The normalized count rates of the gamma ray detector are then characterized with respect to a relative velocity between the water and the detector. The step of characterizing is performed in portions of the conduit which are sloped so that gravity acts on the water along the predetermined direction. A fraction of the characterized counting rate represented by the oxygen activation counting rates measured along the conduit is then determined. The fraction of the characterized counting rate represented by the measured counting rate is the fractional volume of water moving in the predetermined direction.

In the preferred embodiment of the invention, the fractional volume of water occupying the conduit is determined by measuring spectra of neutron induced inelastic gamma rays of the fluid in the conduit.

The invention includes a production logging apparatus for measuring a volume fraction of water moving in a predetermined direction along a highly inclined wellbore. The apparatus includes a controllable-duration source of high energy neutrons, a first gamma ray detector spaced apart from the source at a distance adapted to measure neutron-induced inelastic gamma ray spectra, a second gamma ray detector spaced further apart from the source than the first detector at a distance adapted to measure oxygen activation gamma radiation and a third gamma ray detector spaced further apart from said source than the second detector at a distance adapted to measure oxygen activation radiation. The second and the third detectors are spaced apart at distances for measuring oxygen activation velocity of water. The apparatus includes signal processing circuits for counting neutron induced inelastic gamma rays detected by said first detector and resolving the energy spectra of the inelastic gamma rays so detected. The signal processing circuits also count oxygen activation gamma rays detected by the second and the third detectors.

DESCRIPTION OF THE PREFERRED EMBODIMENT

Figure 1:
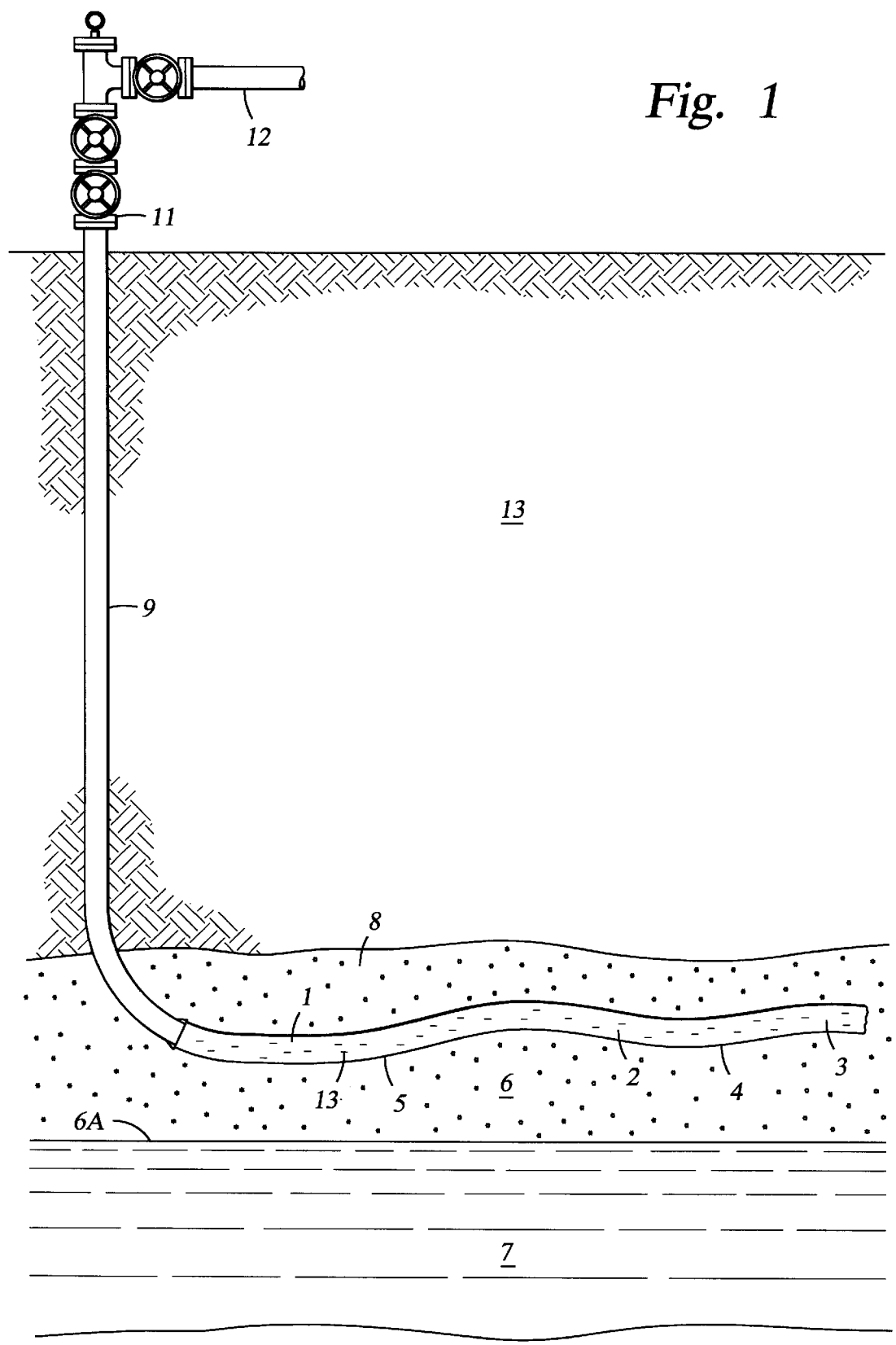
FIG. 1 shows a typical horizontal wellbore drilled through a petroleum-bearing zone in a reservoir.

A highly inclined or horizontal wellbore is shown generally at 1 in FIG. 1. The wellbore 1 is typically drilled substantially vertically near the earth's surface but is inclined nearly horizontally where it penetrates a petroleum-bearing zone 6 in a reservoir 8. The wellbore 1 is drilled nearly horizontally in the petroleum-bearing zone 6 to increase the effective length of the wellbore 1 through the petroleum-bearing zone 6 while minimizing the hydraulic effect of the wellbore 1 upon a water-bearing zone 7 located generally beneath an oil/water contact 6A. The oil/water contact 6A, as is well known in the art, is the result of segregation of the petroleum and the water by gravity, and it is to be understood that the contact 6A could also be any other gravity segregation contact, including a gas/water contact or an oil/gas contact. The wellbore 1 may include a pipe or casing 9 to hydraulically isolate earth formations 13 which are not intended to contribute to the fluid production from the wellbore 1 and to maintain the mechanical integrity of the wellbore 1.

Fluids which generally include petroleum and may include various amounts of water are shown entering the wellbore at 13, and flowing generally in a direction towards a wellhead 11 coupled to the end of the casing 9 at the earth's surface. The wellhead 11, as is known in the art, can include various valves for controlling the amount of the fluids 13 which exit the wellbore 1 and are discharged into a flowline 12. The description of this invention will refer to fluid flowing in a direction so as to exit the wellbore 1 at the wellhead 11 as flowing in the direction of the wellhead 11.

It can be seen in FIG. 1 that the wellbore 1 includes some segments, such as shown at 4 and 5, where the inclination of the wellbore 1 exceeds 90°, meaning that the true vertical depth of the wellbore 1 is decreasing even as the measured depth of the wellbore 1 is increasing. While drilling a horizontal or highly inclined wellbore it is frequently necessary to drill the wellbore 1 at such inclination to maintain the trajectory of the wellbore 1 above the oil/water contact 6A. As the desired trajectory is restored, the inclination may then be reduced to 90° or below, these sections of the wellbore 1 being shown at 2 and 3. It should be noted that the amount of inclination change shown at 2, 3, 4, and 5 in FIG. 1 is greatly exaggerated in vertical appearance for purposes of explaining the invention. Nonetheless, segments of the wellbore 1 such as between 2 and 4 make efficient traps for any water in the fluids 13 flowing towards the wellhead 11 because the water tends to segregate towards the bottom of the wellbore 1 by gravity.

In some cases, the flowing water may include gravity-induced internal turbulences which cause a portion of the total volume of water in the wellbore 1 either to be stagnant or to actually be moving in a direction away from the wellhead 11, even though the aggregate, or net, water flow is in a direction towards the wellhead 11. It is important to the wellbore operator to be able to determine the rate at which water is actually flowing in the direction of the wellhead 11 at any position in the wellbore 1 so that portions of the wellbore 1 which contribute to the water production may be closed off or otherwise appropriately controlled. Stagnant or reverse flowing water in the "traps" has made it difficult to determine the actual rate at which water is flowing towards the wellhead 11.

Figure 2:
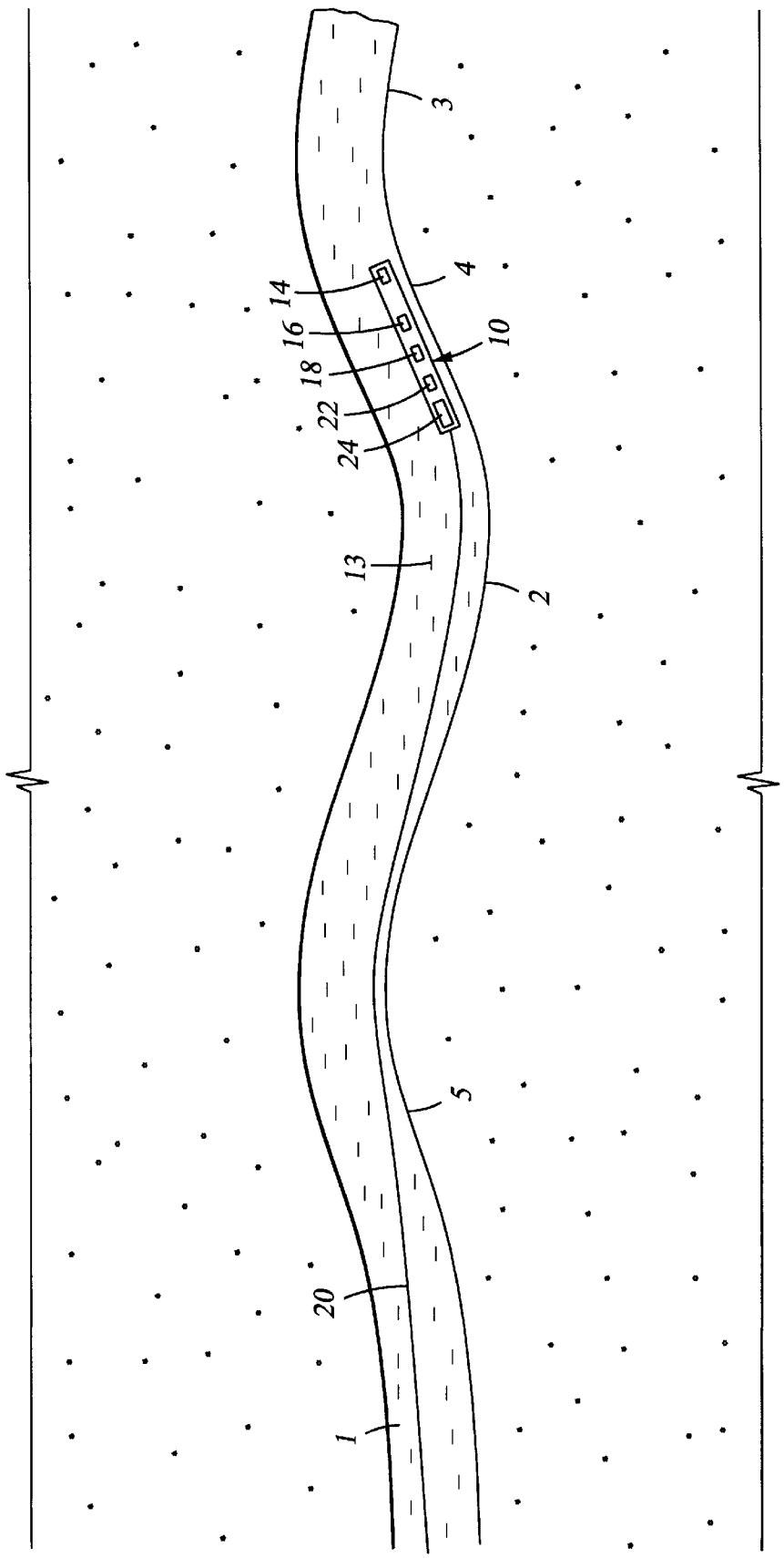
FIG. 2 shows a production logging instrument performing logging measurements according to the invention.

Referring now to FIG. 2, the horizontal portion of the wellbore 1 is shown in more detail. Also shown in FIG. 2 is a production logging instrument 10 suitable for making measurements for the method of this invention. The production logging instrument 10 can include a controllable-duration source of high energy neutrons, such as one described in U.S. Pat. No. 4,996,017 issued to Ethridge, for example. The production logging instrument 10 can also include gamma ray detectors at spaced apart locations from the source 14: a near detector 16, a center detector 18 and a far detector 22. The detectors 16, 18, 22 can be electrically coupled to a pulse height, or spectral, analyzer (not shown separately) forming part of a telemetry/controller unit 24. The telemetry/controller unit 24 includes circuits for periodically actuating the source 14 to cause the source 14 to emit short duration "bursts" of high energy neutrons into the fluids 13 in the wellbore 1. The detectors 16, 18, 22 are arranged so that center 18 and far 22 detectors are appropriately spaced from the source 14, and their detection is timed by the telemetry/controller unit 24 to count gamma rays resulting from neutron activation of oxygen in the fluids 13. These gamma rays are specifically detected for the purpose of measuring the velocity of water in the fluids 13. Suitable spacings and timing features are described, for example in U.S. Pat. No. 5,404,752 issued to Chace et al.

The spacing and timing of the near detector 16 and the center detector 18 are preferably suited for measuring the volume fractions ("holdups") of oil, gas and water in the fluids. Timing and spacing the detectors 16, 18 to measure holdups from gamma ray detection is described in a paper entitled, "Measuring Three-Phase Holdups in Horizontal Wellbores Using Pulsed Neutron Instruments", D. Trcka et al, Society of Petroleum Engineers, Richardson, Tex., paper no. 36561(1996). Generally speaking, the holdups are determined from the energy spectra of so-called "inelastic" gamma rays detected during neutron "bursts" (during the time the source 14 is energized). It should be noted that the instrument 10 shown in FIG. 1 is capable of measuring both the gamma rays necessary to determine holdup and oxygen activation gamma rays used to measure water velocity in a single trip of the instrument 10 along the wellbore 1. The gamma rays thus detected can be measured and recorded for processing according to the method of the invention.

The measurements of gamma rays made by each detector 16, 18, 22 can be transmitted to the earth's surface over an electrical logging cable 20, or may also be stored in an appropriate recording device (not shown) in the telemetry/controller unit 24. It will be readily appreciated by those skilled in the art that the logging instrument 10 must be conveyed along the horizontal portion of the wellbore 1 by a means other than gravity in order to move it away from the wellhead (11 in FIG. 1). Such conveyance methods are well known in the art and are not shown here for clarity of the description of the invention, as the manner of conveyance of the production logging instrument 10 does not affect the method of this invention.

While the production logging instrument 10 shown in FIG. 2 includes detectors 16, 18 suited for making pulsed neutron-type measurements of water velocity and holdups, it should be clearly understood that the method of this invention does not require pulsed neutron-type measurements of the holdups. Any other suitable instrument for measuring holdup, such as capacitance sensors or fluid density sensors, can be used with the method of this invention. See for example, "Interpretive Methods for Production Well Logs", Western Atlas Logging Services, Houston, Tex. (1982), p. 87 for a description of a fluid density sensor, and pp. 99–100 for a description of a capacitance sensor. It should be noted, however, that the pulsed neutron-type measurement of holdup has particular advantages when used in highly inclined or horizontal wellbores, as is described in the Trcka et al reference, supra. Specifically, the fluids in the wellbore 1 tend to segregate by gravity, so sensors which measure only a localized holdup in the immediate vicinity of the sensor may provide erroneous holdup readings if the localized holdup is not representative of the aggregate fluid composition in the wellbore 1.

The method of the invention will now be explained. First, the velocity of water in the wellbore 1 can be measured by counting oxygen activation gamma rays at the center 18 and far 22 detectors. U.S. Pat. No. 5,404,752 issued to Chace et al, for example, describes one method for determining the flow velocity of water using oxygen activation gamma ray measurements. The velocity of water is generally related to oxygen-activation gamma ray counting rates (CR) made a particular one of two gamma ray detectors (and in this invention particularly at the center 18 and far 22 detectors on the instrument 10 shown in FIG. 2) by an expression similar in form to the following:

$$CR = \frac{A}{v}\exp\left(\frac{-\lambda B}{v}\right) \quad (1)$$

where A and B represent constants related to the diameter of the wellbore and the spacings of each of the detectors 18, 22 from the neutron source 14. v represents the relative velocity of the water flowing past the instrument 10 in the direction from the neutron source to the particular detector, and $\lambda$ represents the decay constant for oxygen-16. The velocity of the instrument 10 can be determined using measurements of the cable speed, or any similar method known in the art. Constants A and B can be determined for each detector 18, 22 to characterize the oxygen-activation gamma ray count-ing rate ("counting rate") at each detector 18, 22 with respect to relative water flow rate with respect to the instrument 10. The reason that the counting rates are thus characterized for two differently spaced detectors is that the relationship between the counting rate and the relative flow rate at each detector does not have a unique value of counting rate for each value of relative flow rate (refer to FIG. 3 of the Chace et al '752 patent for an illustration of the counting rate/relative flow rate relationship). By characterizing the counting rate with respect to flow rate at two differently spaced detectors, two values of counting rate can determine one unique value of relative flow rate. Using this part of the method described in the Chace et al '752 patent, or any similar method for determining water velocity using oxygen activation radiation measurements, the water velocity relative to the instrument velocity can be determined from the gamma ray counting rates from both the far 22 and center 18 detectors. The absolute water velocity can then be determined from the relative water velocity and the instrument velocity.

The absolute counting rate of the oxygen activation gamma-rays at the detectors 18, 22 will also be affected, however, by the water holdup (volume fraction of water) present at the location where the relative water velocity is measured. Because oil and gas emit substantially no oxygen activation gamma radiation, the oxygen activation gamma ray counting rate, at any particular relative water velocity, will be a fraction of the oxygen activation gamma ray count rate which would obtain at 100% water holdup for that particular relative water velocity. This can be shown by the following expression:

$$CR_{actual} = H_w \times CR_{Hw=1.0} \quad (2)$$

where $CR_{actual}$ represents the measured oxygen activation gamma ray counting rate, $H_w$ represents the water holdup and $CR_{Hw=1.0}$ represents the detector oxygen activation gamma ray counting rate which would obtain if the water holdup were 100% at that relative water velocity. Equation (2) is linear, but it should be clearly understood that the relationship between the measured gamma ray count rate and the count rate which would obtain at 100% water holdup may be shown by laboratory experimentation to be best represented by another type or ordered relationship. Therefore the invention is not to be limited to determining the count rate which would obtain at 100% water holdup by linear scaling.

Equation (2) can be solved for the 100% water holdup count rate ($CR_{Hw=1.0}$) for different values of relative water velocity, v, as measured throughout the wellbore 1, by scaling the measured oxygen activation gamma ray counting rates from either one of the detectors 18, 22 used to measure the relative water velocity. The water holdup itself can be obtained using the gamma rays measured from the near 16 and/or the center 18 detectors, or from any other suitable device for measuring water holdup, as previously explained. In the invention, a "characteristic count rate curve" can be determined which relates the relative water velocity to oxygen activation count rate which would obtain at either the center 18 or far 22 detector, for the case where the water holdup is 100%. If in addition, each of the relative water velocity measurements used to determine the characteristic count rate curve is made at a location in the wellbore where the inclination is greater than 90°, such as shown at 4 and 5 in FIG. 2, then the characteristic count rate curve will be determined for the case where substantially all of the water is moving in the direction of the wellhead (11 in FIG. 1). The water in these portions 4, 5 of the wellbore 1 is assumed to be substantially all moving towards the wellhead 11 because in these portions 4, 5 of the wellbore 1 gravity has a component acting on the water flow in the same direction as the fluid 13 flow. These so-called "downsloping" portions 4, 5 of the wellbore 1 can be identified from a directional survey obtained from the drilling operator, or may be determined by measurements made by the logging instrument itself using a directional survey system (not shown) of any type suitable for use with well logging instruments. Such directional survey systems are well known in the art.

Figure 3:
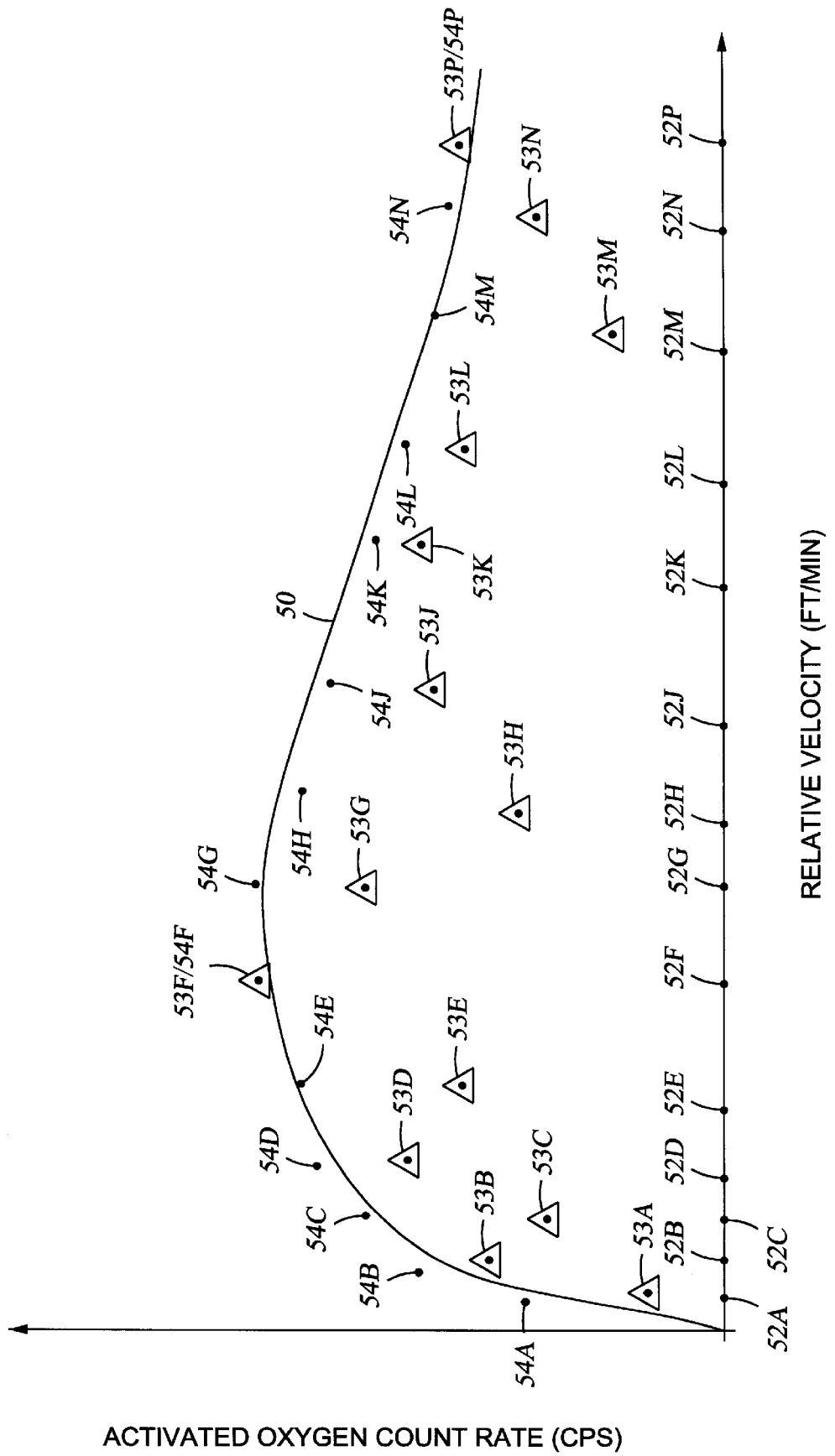
FIG. 3 shows a graph of gamma ray counting rates from a detector used to generate a "characteristic flow rate curve" for the instrument in FIG. 1.

FIG. 3 illustrates the determination of the characteristic count rate curve for the production logging instrument (10 in FIG. 1). As the instrument 10 is moved through the wellbore (1 in FIG. 1), the water velocity relative to the instrument velocity can be determined from oxygen activation as previously explained, particularly in the "downsloping" portions of the wellbore (such as 4, 5 in FIG. 2). The relative water velocity values thus determined are shown on the coordinate axis of the graph in FIG. 3 at 52A through 52P. For each relative velocity value, at the same location where the relative velocity value is determined, a water holdup can also be determined using the pulsed neutron method previously described, or any other suitable method. Points representing the value of the counting rate for one of the detectors (preferably the center detector 18 on the instrument of FIG. 1 for reasons of statistical precision) at each value of relative water velocity are shown at 53A through 53P. The ordinate value of each of the points 53A–53P can then be scaled with respect to the locally measured value of water holdup, using the relationship from equation (2) or a laboratory-derived ordered relationship as previously explained. The scaled ordinate values represent the detector count rates which would obtain if the water holdup were 100%. These values are shown plotted as points 54A through 54P at the same relative water velocities 52A–52P. At velocity points 52F and 52P, the absolute counting rate 53F, 53P respectively is shown as the same value as the "scaled" counting rate 54F, 54P because these points represent locations in the wellbore (1 in FIG. 2) where the water holdup is 100%.

A best fit curve, in a form similar to that described by equation (1), can then be fitted through the scaled ordinate values (points 54A–54P) using least squares or other error minimization technique known in the art. This curve, shown at 50, represents the "characteristic count rate curve" for the particular logging instrument in the particular wellbore being surveyed.

Since all the relative velocities used to determine the characteristic curve 50 were determined where substantially all the water is moving towards the wellhead (11 in FIG. 1) the oxygen activation gamma ray counting rates actually measured at the same detector (preferably, as previously explained, the center detector 18 on the instrument shown in FIG. 1) can be used to determine a relative fraction of water, $H_w$(uphole) which is moving towards the wellhead (11 in FIG. 1) at any other location along the wellbore (1 in FIG. 1) simply by calculating the fraction of the ordinate value of the characteristic curve 50, $CR_{characteristic}$, represented by the count rate, $CR_{measured}$, of the center detector 18 at the position of interest. As shown in the following expression: Multiplying that fraction, $H_w$(uphole) by the water velocity, v, determined from the center 18 and far 22 detector count rates as previously explained, can provide a $$H_w(\text{uphole}) = \frac{CR_{measured}}{CR_{characteristic}} \quad (3)$$

calculation of the total volumetric flow rate of water towards the wellhead (11 in FIG. 1). It should be noted that if the center detector 18 is used to measure oxygen activation gamma rays, it may also be used to measure inelastic gamma rays emitted during one of the neutron bursts. This may be accomplished by programming the telemetry/controller unit (24 in FIG. 2) to spectrally analyze and count gamma rays measured by the center detector 18 during the neutron bursts, as well as counting gamma rays detected during a so-called "late background" counting period in which gamma rays having the characteristic energy spectral signature (about 6.1 MeV) of activated oxygen are likely to be present.

Those skilled in the art will devise other embodiments of the invention which do not depart from the spirit of the invention as disclosed herein. Accordingly the invention should be limited in scope only by the attached claims.

What is claimed is:

1. A method for determining a volume fraction of water moving in a predetermined direction along a highly inclined conduit, comprising:

measuring a fractional volume of water occupying said conduit at a plurality of locations along said conduit;

measuring an oxygen activation velocity of water flowing in said conduit at a plurality of locations along said conduit;

measuring oxygen activation gamma radiation and normalizing a counting rate of a gamma ray detector used for said measuring oxygen activation gamma radiation with respect to said measured fractional volume of water;

characterizing said normalized count rate of said gamma ray detector with respect to a relative velocity between said water and said detector, said step of characterizing performed in portions of said conduit sloped so that gravity acts on said water along said predetermined direction; and determining a fraction of said characterized counting rate represented by said measured oxygen activation gamma radiation counting rates measured along said conduit.

2. The method as defined in claim 1 wherein said fractional volume of water occupying said conduit is determined by measuring pulsed neutron induced inelastic gamma ray spectra of said fluid in said conduit.

3. The method as defined in claim 1 wherein said step of measuring said oxygen activation velocity comprises determining a relationship between a velocity of water and a gamma ray counting rate for each of two different spaced apart locations from a source of neutrons and determining a value of said velocity which corresponds to counting rates measured at each said spaced apart locations.

4. A production logging apparatus for measuring a volume fraction of water moving in a predetermined direction along a highly inclined wellbore, comprising:

a controllable-duration source of high energy neutrons;

a first gamma ray detector spaced apart from said source at a distance adapted to measure neutron-induced inelastic gamma ray spectra;

a second gamma ray detector spaced further apart from said source than said first detector at a distance adapted to measure oxygen activation gamma radiation;

a third gamma ray detector spaced further apart from said source than said second detector at a distance adapted to measure oxygen activation radiation, said second and said third detectors spaced apart at distances for measuring oxygen activation velocity of water; and signal processing circuits for counting neutron induced inelastic gamma rays detected by said first detector and resolving energy spectra thereof, and for counting oxygen activation gamma rays detected by said second and said third detectors.

5. The apparatus as defined in claim 4 wherein said signal processing circuits count neutron induced inelastic gamma rays detected by said second detector and resolving energy spectra thereof.

\* \* \* \* \*